(12) United States Patent
Shimura et al.

(10) Patent No.: US 7,238,657 B2
(45) Date of Patent: *Jul. 3, 2007

(54) CARTILAGE/BONE INDUCING MATERIALS FOR PREPARATION

(75) Inventors: Takesada Shimura, Saitama (JP); Satsuki Toriyama, Saitama (JP)

(73) Assignee: Biopharm Gesellschaft zur Biotechnologischen Entwicklung Von Pharmaka mbH, Heidelberg (DE)

( * ) Notice: Subject to any disclaimer, the term of this patent is extended or adjusted under 35 U.S.C. 154(b) by 149 days.

This patent is subject to a terminal disclaimer.

(21) Appl. No.: 10/885,099

(22) Filed: Jul. 7, 2004

(65) Prior Publication Data

US 2005/0013864 A1 Jan. 20, 2005

Related U.S. Application Data

(62) Division of application No. 09/068,253, filed as application No. PCT/JP96/03333 on Nov. 14, 1996, now Pat. No. 6,903,071.

(30) Foreign Application Priority Data

Nov. 17, 1995 (JP) ................................. 7-322402

(51) Int. Cl.
  *A61K 38/17* (2006.01)
  *A61K 38/00* (2006.01)
(52) U.S. Cl. ........................... 514/2; 514/21; 530/333; 530/354; 435/69.4
(58) Field of Classification Search .................. 514/2, 514/21; 530/333, 354; 435/69.4
See application file for complete search history.

(56) References Cited

U.S. PATENT DOCUMENTS 4,863,732 A 9/1989 Nathan et al.
5,292,802 A 3/1994 Rhee et al.
5,902,785 A * 5/1999 Hattersley et al. ............. 514/2
6,903,071 B2* 6/2005 Shimura et al. ............. 514/12

FOREIGN PATENT DOCUMENTS

| JP | 61277612 | 12/1986 |
| JP | 62135431 | 6/1987 |
| JP | 1265968 | 10/1989 |
| JP | 6508777 | 10/1994 |
| WO | WO 9300050 A1 | 1/1993 |
| WO | WO 9621427 | 1/1996 |
| WO | WO 9401483 | 3/1996 |

* cited by examiner

*Primary Examiner*—Jon Weber
*Assistant Examiner*—Abdel A. Mohamed
(74) *Attorney, Agent, or Firm*—Rothwell, Figg, Ernst & Manbeck

(57) ABSTRACT

A cartilage and bone morphogenetic repairing composition which contains a bone morphogenetic protein and a polyoxyethylene-polyoxypropylene glycol is disclosed. It is preferable that the molecular weight of a polyoxypropylene, i.e., a component of said polyoxyethylene-polyoxypropylene glycol, is in the range of about 1,500-4,000 and the weight ratio of ethylene oxide is in the range of 40-80%/molecule, and a concentration of said polyoxyethylene-polyoxypropylene glycol in an aqueous solution is about 10-50%. The composition may be applied in a cartilage and bone morphogenetic method without a surgical operation and comprises a bone morphogenetic protein and a carrier which has a high bio-absorption, a good affinity to the bone morphogenetic protein and is capable of temperature dependent gel-sol reversible transition. The composition may conveniently be applied locally to the site of a bone fracture or bone defect.

14 Claims, 4 Drawing Sheets

US 7,238,657 B2

CARTILAGE/BONE INDUCING MATERIALS FOR PREPARATION

CROSS REFERENCE TO RELATED APPLICATION

This application is a divisional application of U.S. application Ser. No. 09/068,253, filed Jun. 9, 1998, now U.S. Pat. No. 6,903,071, which was filed under 35 U.S.C. § 371 of PCT/JP96/03333 filed Nov. 14, 1996, the disclosure is hereby incorporated by reference.

FIELD OF THE INVENTION

The present invention relates to a cartilage and bone morphogenetic repairing composition for the treatment of bone fracture and bone defect. In more detail, this invention is concerned with the cartilage and bone morphogenetic repairing composition which contains a polyoxyethylene-polyoxypropylene glycol and a bone morphogenetic protein.

BACKGROUND OF THE INVENTION

For repairing cartilages and bones, in addition to autoplasty, there has been practiced a procedure in which a prosthetic material for defected sites of cartilage and bone composed of a combination of a bone morphogenetic protein and a suitable carrier was imbedded in the defected site. In practicing this, the defected site can be exposed on surgical operation to apply a cartilage and bone repairing composition containing a bone morphogenetic protein directly to the defected site, and thus, the materials in a solid form such as blocks, sponges, sheets and the like which are easy to handle have been widely applied. Those in a semisolid form such as gels or pastes can also be used. As the carriers which made such solid or semisolid forms applicable, there have been utilized, for example, metals such as stainless or titanium alloys or collagen and hydroxyapatite (HAP) or a mixture thereof.

On the other hand, an attempt has been made to administer a bone morphogenetic protein for the treatment of bone fracture or osteoarthritis without requiring any surgical operation. This administration mode has been earnestly desired from a viewpoint that non-invasive administration, namely, injection mode, would alleviate pains from patients. However, the injection route of a simple aqueous liquid preparation of a bone morphogenetic protein causes diffusion and disappearance of the drug after administration, and so in order to achieve an effective administration, the bone morphogenetic protein should be retained in the injected site over a certain period of time. In view of the above, there has been envisaged a carrier which may be in a liquid state capable of passing through a needle on administration and then phasetransited to a gel-like state after administration to retain the bone morphogenetic protein in the injected site. Preferably, the carrier may have non-toxicity, a good biocompatibility and a high bio-absorption in a living body.

Collagen is a known carrier for a bone morphogenetic protein and is confirmed to possess favorable bio-compatibility and bio-absorption (Japanese Patent Publication No. 75425/1993). Collagen with an injectable character has also been reported, which may provide an injectable cartilage and bone morphogenetic material (Japanese Patent Publication Nos. 23322/1995 and 53140/1993). However, collagen now available for the use of medicines is derived from natural sources such as cattle or a pig, so that its properties such as a molecular weight, an amino acid composition and a moisture holding property are not always constant. In addition, it has some side-effects such as antigenicity because it is a heterologous protein to humans. In particular, antigenicity cannot be completely eliminated even when atelocollagen; i.e., collaged from which teropeptide sites are removed, is used (J. American Academy of Dermatology 10, 638-646 and 647-651, 1984 and ibid, 21 1203-1208, 1989).

On the other hand, it was reported that biodegradable polymers such as polylactic acid or polylactic acid-glycolic acid copolymers can be used as pharmaceutical carriers (U.S. Pat. No. 5,385,887 and Japanese Patent Publication No. 22570/1994). However, the biodegradable polymers are in a solid or semisolid state which may maintain a given form, and in view of this, they are classified as a group of applicable materials to surgical operation. Even if an injectable complex can be prepared using such biodegradable polymers, an organic solvent should be employed during the preparation process, which may easily anticipate the problem of inactivation of the active ingredient, a bone morphogenetic protein.

DETAILED DESCRIPTION OF THE INVENTION

It is an object of this invention to provide a cartilage and bone morphogenetic repairing composition, which can overcome the prior art disadvantages or drawbacks as discussed above, which have a high bio-absorption and a good affinity to the active ingredient or a bone morphogenetic protein, and which show the sustained disposition of a bone morphogenetic protein by causing a temperature dependent sol-gel reversible transition with less side-effects such as antigenicity and so on.

The present inventors have made earnest studies on the relationship between the active ingredient, a bone morphogenetic protein, and a carrier therefore in the case of a bone repairing method without surgical operation and have found that a certain class of polyoxyethylene-polyoxypropylene glycols can show a high bio-absorption, a good affinity to a bone morphogenetic protein and temperature dependent sol-gel reversible transition. The present inventors have prepared a bone morphogenetic composition by mixing an aqueous polyoxyethylene-polyoxypropylene glycol solution and a bone morphogenetic protein, which is an injectable liquid at a temperature of from 1° C. to 30° C. at the time of administration and may be gelatinized at around 37° C. within 3 minutes after administration. It has been found that ectopic cartilage and bone morphogenesis are accomplished by administering said composition to mice intramuscularly at the femoral muscle and then retaining a bone morphogenetic protein at the administration sites in vivo upon which this invention has been completed.

This invention is concerned with a cartilage and bone morphogenetic repairing composition which contains a polyoxyethylene-polyoxypropylene glycol and a bone morphogenetic protein.

The polyoxyethylene-polyoxypropylene glycol(s) as used herein is a generic name of nonionic surface active agents of a polymer type having less hydrophilic polyoxypropylene as a hydrophobic group and ethylene oxide as a hydrophilic group. It may be feasible to prepare surface active agents having various properties by changing a molecular weight of the polyoxypropylene and a mixing a ratio thereof to the ethylene oxide. The synthesizable-polyoxyethylene-polyoxypropylene glycols have a molecular weight of the polyoxypropylene glycol in the range of 900-4,000 and a percent by weight of the ethylene oxide in the total molecule of 5% to 90%. For instance, the polyoxyethylene-polyoxyopropylene glycol block polymers (ADEKA®) manufactured by Asahi Denka Kogyo K.K. are systematically named according to a molecular weight of polyoxypropylene glycol and a weight ratio of the ethylene oxide to be added and the classification list thereof is shown in FIG. 1.

Industrial utilization of polyoxyethylene-polyoxypropylene glycols includes aperients, ointment bases, artificial blood, coating for tablets, excipients, solubilizers or solubilizing agents for injections and others in the field of pharmaceutics, in addition to the use as general cleaning agents or antifoamings. In particular, Pluronic F-68 (a molecular weight of polyoxypropylene of 1,750 and an ethylene oxide content of 80%) has a remarkable antihemolytic action and has been marketed in the name of EXOCORPOL® from the Green Cross Corporation (polyoxyethylene-polyoxypropylene glycol) as an additive for extracorporeal circulation of blood. It is apparent from the results of toxicity tests using various animals that polyoxyethylene-polyoxypropylene glycols have extremely low toxicity and low irritative property, with no reports on possible side-effects such as antigenicity and so on (Fragrance Journal, 7, 82-87, 1974). The results of toxicity tests are shown in Table 1.

TABLE 1

Results of acute toxicity tests using ADEKA ® Pluronics

| ADEKA ® Pluronics | Animal Species | $LD_{50}$(g/kg) |
|---|---|---|
| L-44, L-62, L-64 | Rats | 5 |
| F-68 | Mice | >15 |
| F-68 | Rats, Rabbits, Dogs | No acute toxicity |
| P-85 | Rats | 34.6 |

Polyoxyethylene-polyoxypropylene glycols are superior in terms of handiness to collagen showing non-reversible phase-transition by changes in temperatures in the point that they show reversible sol-gel phase-transition. This property may be controlled by selection of the optimum polyoxyethylene-polyoxypropylene glycol for the temperature to develop the phase transition and by changing the concentration of the aqueous solution of said polyoxyethylene-polyoxypropylene glycol (Int. J. Pharm. 22, 207-218, 1984 and EP 0551626A1).

It is obvious from the foregoing that polyoxyethylene-polyoxypropylene glycols have a superior nature as a drug carrier. Attempts have already been made to combine them with a low molecular weight drug such as local anesthetics, anticancer agents and so on (Int. J. Pharm. 8, 89-99, 1981 and Chem. Pharm. Bull. 32, 4205-4208, 1984) and to admix with a high molecular weight physiologically active protein such as interleukins and the like (Pharm. Res. 9, 425-434, 1992).

This invention relates to a cartilage and bone morphogenetic repairing material which contains a polyoxyethylene-polyoxypropylene glycol and a bone morphogenetic protein, wherein the polyoxypropylene as a constituent of said polyoxyethylene-polyoxypropylene glycol has a molecular weight of about 1,500-4,000 and an ethylene oxide content of about 40-80% molecule. Within the above ranges, there will be provided the Pluronics capable of performing temperature dependent sol-gel reversible transition, which characterized the present Pluronics.

Moreover, this invention relates to a cartilage and bone morphogenetic repairing composition wherein a concentration of polyoxyethylene-polyoxypropylene glycols as described above in an aqueous solution is about 10-50%. It is known that the reversible phase transition temperature of polyoxyethylene-polyoxypropylene glycols varies in general depending on the concentration of their prepared aqueous solutions, and the polyoxyethylene-polyoxypropylene glycols within the above-mentioned constituent ranges may gelate at around body temperature, i.e. about 37° C. at a temperature of about 10-90% in its aqueous solution. As the most preferable example, there is prepared the polyoxyethylene-polyoxypropylene glycol block polymer aqueous solution of 15-30% concentration having a molecular weight of polyoxypropylene of 3,850 and an ethylene oxide content of 70% (Pluronic F-127).

The bone morphogenic protein (BMP) as used herein is the protein having an activity to induce undifferentiated mesenchymal cells to cartilage cells, thereby performing bone morphogenesis.

The bone morphogenetic proteins used in this invention include, but are not limited to, a series of proteins belonging to the TGF β gene superfamily such as BMP-2 to BMP-9 and so on, the protein named MP52, the protein named GDF-5 and the like. Particularly preferable BMP-2 is a protein produced using Chinese hamster ovary (CHO) cells according to the genetic engineering technology reported by Wang, et al. (Proc. Natl. Acad. Sci. USA, 87, 2220-2224, 1990 and U.S. patent application Ser. No. 4,877,864), and particularly preferable MP52 is a new protein produced according to the genetic engineering technology suggested by the present inventors (our copending Japanese Patent Application Serial No. 531,621 filed Oct. 20, 1977). This new protein can be produced by constructing a plasmid containing the DNA sequence coding the amino acid sequence as shown in SEQ ID NO.:1 of the Sequence Listing derived from MP52 described in said Japanese patent application and having added the codon coding methionine at the N-terminal of said DNA sequence; transforming the plasmid into E.coli; incubating the E.coli to obtain an inclusion body; and solubilizing and purifying the inclusion body to obtain a monomer protein, which is then dimerized and purified.

An aqueous solution of 15-30% polyoxyethylene-polyoxypropylene glycol block polymer containing as an active ingredient BMP-2 or MP52 was intramuscularly injected to mice at the femoral muscle. MP52 was retained at the administered sites and then an ectopic cartilage and bone morphogenesis ability was observed in vivo.

There has not yet been reported to date an injectable cartilage and bone morphogenetic repairing material comprising a polyoxyethylene-polyoxypropylene glycol in combination with a bone morphogenetic protein which may be useful for repair of cartilage and bone, especially as a treating agent for bone fracture.

The present invention is further concerned with a cartilage and bone repairing agent containing a polyoxyethylene-polyoxypropylene glycol and a bone morphogenetic protein.

Moreover, the present invention is concerned with a method of treatment for cartilage and bone repairing, by which a cartilage and bone morphogenetic repairing composition comprising a polyoxyethylene-polyoxypropylene glycol in combination with a bone morphogenetic protein which may be useful for repair of cartilage and bone, especially as a treating agent for bone fracture.

The present invention is further concerned with a cartilage and bone repairing composition containing a polyoxyethylene-polyoxypropylene glycol and a bone morphogenetic protein.

Moreover, the present invention is concerned with a method of treatment for cartilage and bone repairing, by which a cartilage and bone morphogenetic composition comprising a polyoxyethylene-polyoxypropylene glycol in combination with a bone morphogenetic protein is administered locally to the site of bone fracture or bone defect of human or animal.

DESCRIPTION OF THE PREFERRED EMBODIMENTS

Figure 1:
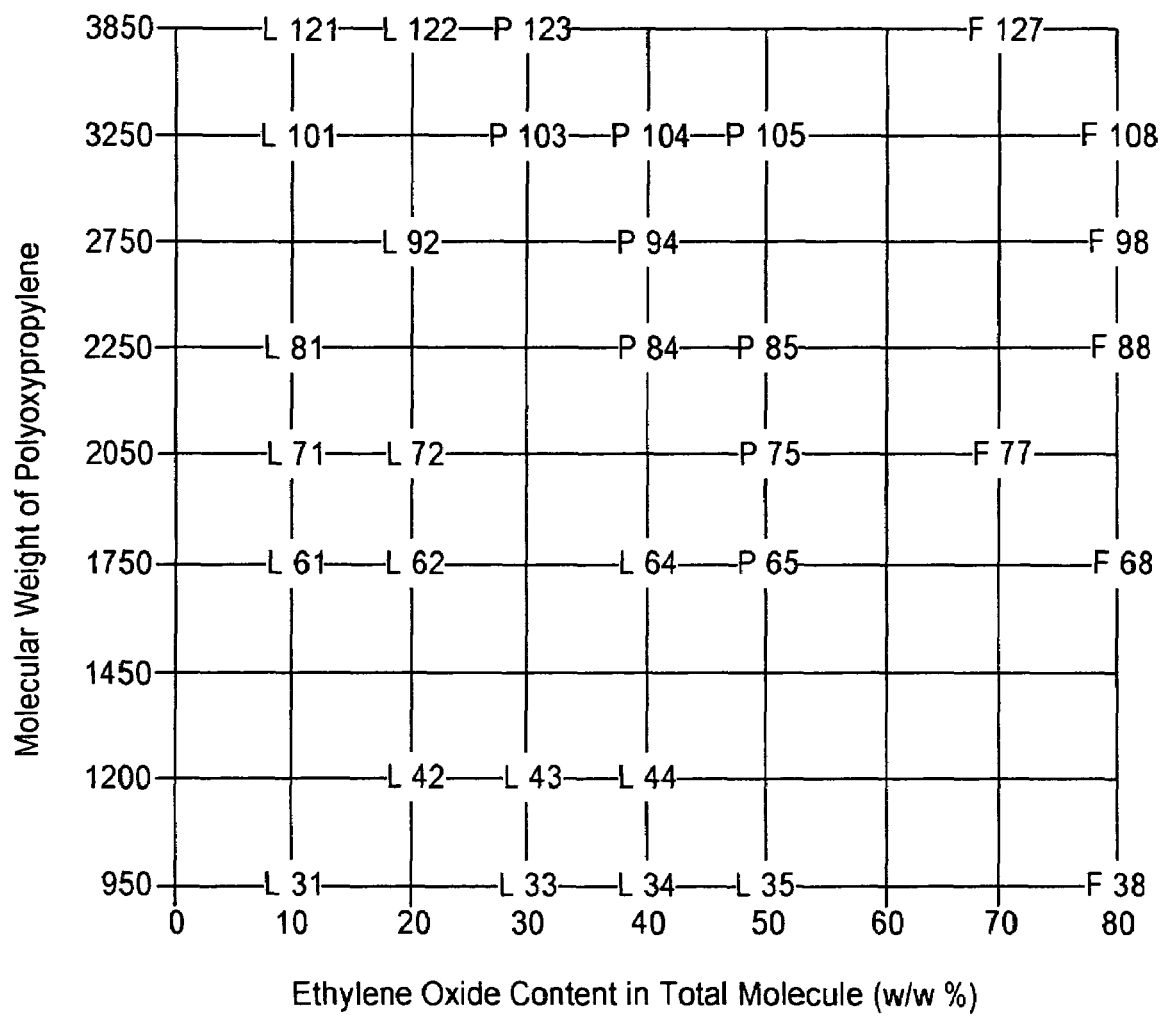
FIG. 1 is a classification figure for AKEDA® Pluronics, wherein an ethylene oxide content in terms of % by weight in a total molecule of a polyoxyethylene-polyoxypropylene glycol is indicated on the abscissa, while a molecular weight of the component polypropylene in a polyoxyethylene-polyoxypropylene glycol is indicated on the ordinate.

The effects of this invention will be illustratively explained by way of the following Examples and Reference Examples. However, this invention is not to be restricted by these Examples.

EXAMPLE 1

Preparation of Cartilage and Bone Morphogenetic Repairing Material Containing BMP-2

ADEKA® Pluronic F-127 (Asahi Denka Kogyo K.K.) is known to be one of the least toxic polyoxyethylene-polyoxypropylene glycols ("SEIYAKU KOJO" 6, 875-880, 1986). In 7.0 g of distilled water for injection was dissolved under ice-cooling 3.0 g of ADEKA® Pluronic F-127 to prepare a 30% aqueous solution of ADEKA® Pluronic F-127. The aqueous solution of ADEKA® Pluronic F-127 was poured potionwise under ice-cooling to a 96-well titer plate at 360 µl/well, 40 µl of 0.01 N HCl containing 80 µg of BMP-2 was added to each well and mixed. The mixture was sterilized by passing through a 0.22 µm filter at 4° C. to form a BMP-2 injection of a total volume of about 400 µl (a final concentration of ADEKA® Pluronic F-127 of 27%). Similarly, the BMP-2 injections having final concentrations of ADEKA® Pluronic F-127 of 10, 15, 18 and 22.25% were prepared.

It was found that injection was feasible at 5° C. or lower in the case of the final concentration of ADEKA® Pluronic F-127 of 27%, at 10° C. or lower in the case of the final concentration of ADEKA® Pluronic F-127 of 22.5%, or at 25° C. or lower in the case of the final concentration of ADEKA® Pluronic F-127 of 10%-18%, while the ADEKA® Pluronic F-127 injection phase-transited to a gel-like state at 37° C. was a preparation having a final concentration of 15% or higher. Accordingly, the most preferable is a preparation of ADEKA® Pluronic F-127 with the final concentration of 18%, which was in a liquid state at room temperature and showed a gelatinized state at 37° C.

EXAMPLE 2

Preparation of Cartilage and Bone Morphogenetic Repairing Material Containing MP52

The MP52 injections having final concentrations of ADEKA® Pluronic F-127 of 10, 15, 18, 22.5 and 27% were prepared according to the same procedure as described in Example 1. The same injectable preparations as described for the case of the BMP-2 was obtained according to MP52; that is to say, the injectable preparations applicable at 5° C. or lower in the case of the final concentration of ADEKA® Pluronic F-127 of 27%, at 10° C. or lower in the case of the final concentration of ADEKA® Pluronic F-127 of 22.5%, or at 25° C. or lower in the case of the final concentration of ADEKA® Pluronic F-127 of 10%-18%.

EXAMPLE 3

Residual Rates of MP52 in vivo After Administration of Cartilage and Bone Morphogenetic Repairing Material The $^{125}$I-labled MP52 injections having the final concentrations of ADEKA® Pluronic F-127 of 8, 22.5 and 27%, which had been prepared following the same method and formulation as Example 2 except that $^{125}$I-labeled MP52 was further added, were intramuscularly administered to male mice (ICR strain, 8 weeks old) under anesthesia at the femur of the right hind leg at 100 µl using a 23 G needle (about 37 KBq $^{125}$I-MP52/site) and then the radioactivity in the right hind leg was counted at 0.5, 2 and 8 hours after administration. The injection of an $^{125}$I-MP52 aqueous solution was used as a are shown in Table 2.

TABLE 2

$^{125}$I-MP52 residual rates at the right hind leg after administration of (ADEKA ® Pluronic F-127 final concentration of 18%) or aqueous liquid preparation

| Time (hr) | Pluronic Preparation | Aqueous Liquid Preparation |
| --- | --- | --- |
| 0.5 | 60.5% | 32.7% |
| 2 | 19.7% | 13.8% |
| 8 | 14.9% | 7.9% |

It was clearly shown in Table 2 that MP52 when polyoxyethylene-polyoxypropylene glycols were used as a pharmaceutical carrier could apparently be retained more as compared with the case where a simple MP52 aqueous solution was injected. Also similar results were obtained using the injection of Example 1.

EXAMPLE 4

Pharmacological Effect on Ectopic Cartilage and Bone Morphogenesis

Figure 2A:
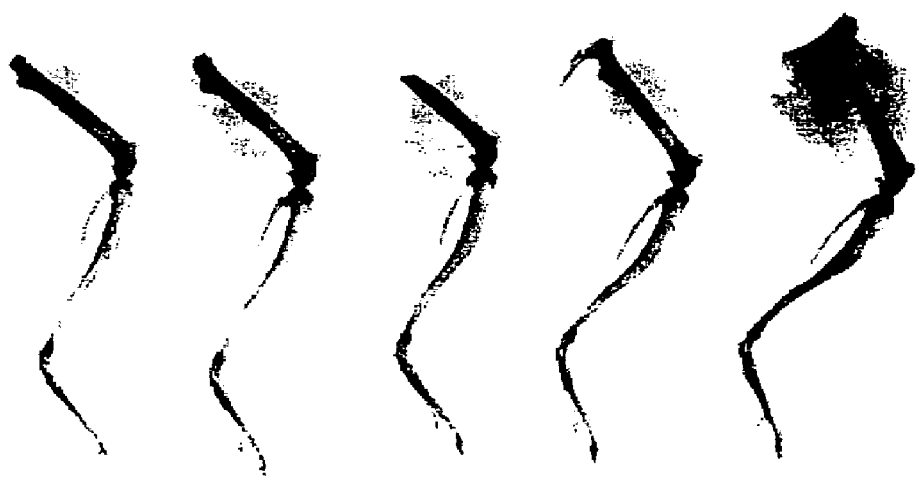
FIG. 2 is soft X-ray photographs of the bone/cartilage calcified tissues of the femur in the right hind leg of the mouse as obtained by Example 4. The photographs (a) and (b) were taken after 2 weeks from the administration of AKEDA® Pluronic F-127 solely and AKEDA® Pluronic F-127 containing MP52, respectively. The apparently blackened parts in the muscle indicate ectopically formed bones.
Figure 2B:

The MP52 injection of ADEKA® Pluronic F-127 final concentration of 18% as prepared in Example 2 was intramuscularly administered to male-mice (ICR strain, 8 weeks old) under anesthesia at the femur of the right hind leg at 100 μl using a 23 G needle (20 μl MP52/site). The ADEKA® Pluronic F-127 injection containing no MP52 was used as a control. Cartilage and bone formation was determined after two weeks from the administration. The mice were sacrificed by vertebral cervical dislocation and the right hind leg of the administration site was cut off and bone formation at the administration site was examined by using a soft X-ray irradiator. The results are shown in FIG. 2 (n=5). As apparent from the soft X-ray images, no shadow was observed in the muscles at the administration site in the case of ADEKA® Pluronic F-127 only (FIG. 2-a), while clear shadow was observed in 80% or more of the animals with ADEKA® Pluronic F-127 containing MP52 (FIG. 2-b).

Figure 3A:
FIGS. 3a and 3b are microscopic photographs of the stained tissues of the non-decalcified sections of the femur of the right hind leg of the mouse as obtained by Example 4. Formations of bone matrices and bone matrices together with osteoblasts and of bone marrows can be confirmed by von-Kossa staining (a) and Hematoxylin-Eosin staining (b), respectively.
Figure 3B:
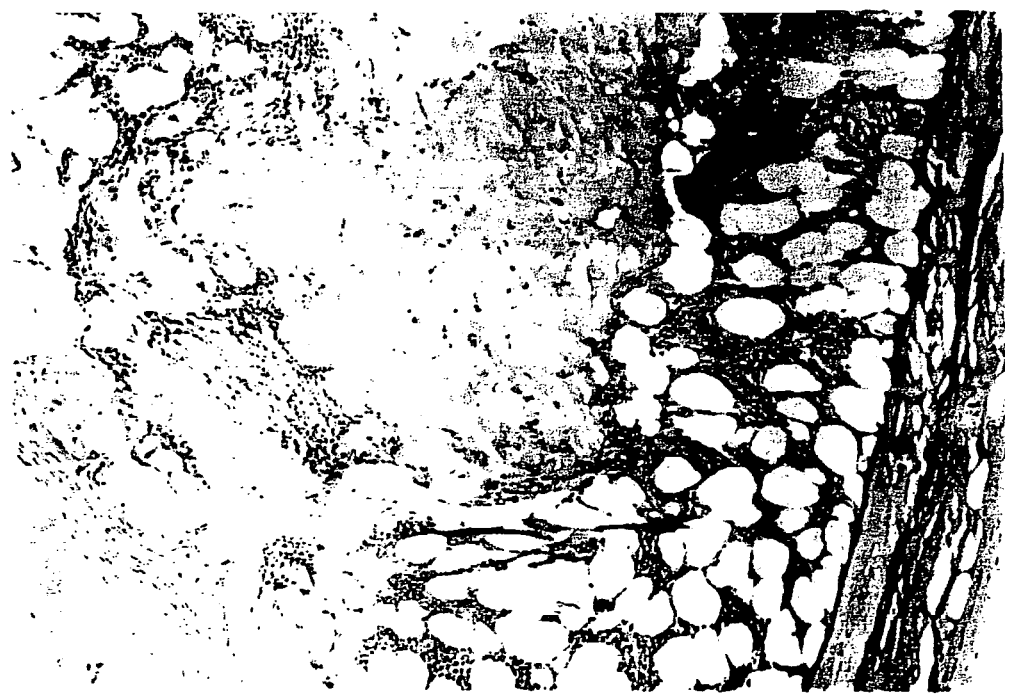

And then, after taking images using soft X-ray, the specimens were kept in 10% formalin and histologic examination was carried out. The microscopic photograph of the stained tissue of the mouse seen at the right end in FIG. 2-b is shown in FIG. 3. In FIG. 3, deposition of calcium was observed at the shadowed portion by von-Kossa staining (FIG. 3-a) and osteoblasts, bone matrices and bone marrows were confirmed by Hematoxylin-Eosin staining (FIG. 3-b), whereby bone formation was confirmed. No inflammatory reaction was observed. In these figures, bone matrix, osteoblast and bone marrow are abbreviated as BM, OB and MA, respectively.

Similar test was carried out using the BMP-2 injection having an 18% final concentration of ADEKA (Pluronic F-127 to give similar results.

From the aforesaid results, safety and usefulness of a polyoxyethylene-polyoxypropylene glycol were confirmed when used as a carrier for the bone forming factor.

REFERENTIAL EXAMPLE

Production of New Protein MP52

1. Construction of Vector (1) Isolation of Variant MP52 Mature Part

Human MP52cDNA was amplified by polymerization chain reaction (PCR) of the mature part only, using the plasmid vector containing cDNA described in WO93/16099 (pSK52s) as a template DNA.

A part of the DNA of the mature type MP52 gene was substituted according to the method for increasing in the productivity of the desired protein by increasing the AT content around the initiation codon ATG (reported by M. Nobuhara et al., Agric. Biol. Chem., 52 (6), 1331-1338, 1988).

Substitution was carried out according to the PCR method using an orthodromic PCR primer of SEQ ID NO.:2. The DNA sequence of the PCR primer utilized the DNA described in SEQ ID.:2 as an orthodromic primer and that described in SEQ ID No.:3 as an antidromic primer. Sequence No.: 2 and No.:5 are those described in the Nobuhara et al reference.

PCR was carried out by adding in the same test tube the template DNA (10 ng), 50 picomoles each of the orthodromic and antidromic PCR primers, DNTP (0.2 mmol) and $MgCl_2$ (1.5 mmol), together with Taq DNA polymerase (5 U).

The PCR of 30 cycles was performed, each cycle comprising denaturation (94° C., one minute) and primer annealing (55° C., one minute) and primer elongation (72° C., 2 minutes). (All the following PCRs were performed under the above-defined conditions.)

The product from the PCR method was separated by electrophoresis in 1.5% low-melting agarose (available from FMC) to cut out the DNA composed of about 360 bp corresponding to the amino acid sequence of SEQ ID NO.:1, which is defined as Fragment 1.

(2) Construction of *E. coli* Expression Vector for the Present Protein

Figure 4:
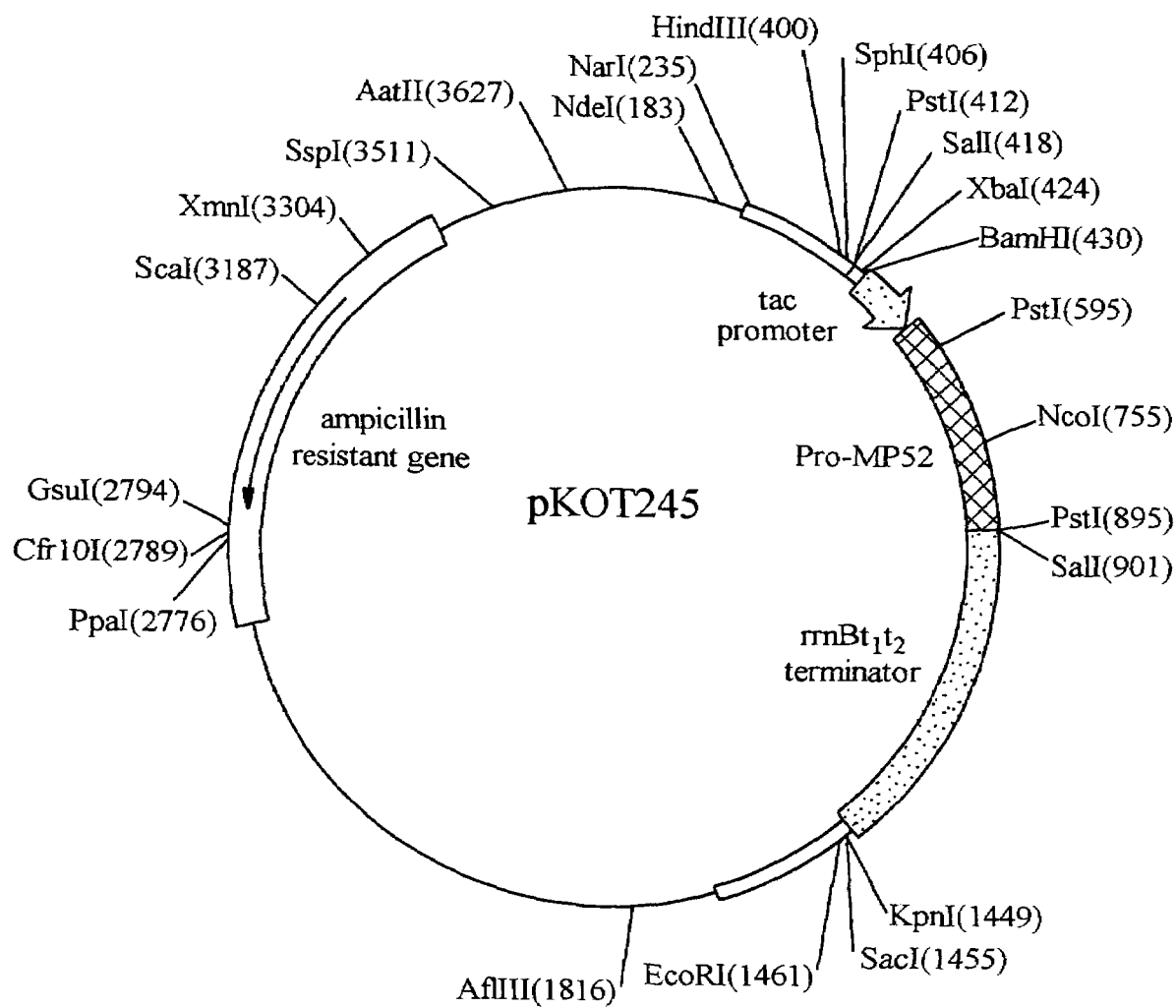
FIG. 4 is a plasmid map of the expression vector of the protein MP52 as obtained by Reference Example 1 (2).

In order to increase the replication number of plasmid, the replication origin was altered from pBR cell to pUC cell line. The tac promoter region of commercially available *E. coli* expression vector pKK223-3 (purchased from Pharmacia Biotech AB) was digested by the restriction enzymes SspI and EcoRI, treated with Mung Bean Nuclease (Takara Shuzo K.K., Catalogue No. 2420A), ligated to the initiation codon site of Fragment 1 with T4DNA Ligase (Takara Shuzo K.K., Catalogue No. 2011A), and the rrnBT$_1$T$_2$ terminator region of pKK223-3 was digested with the restriction enzymes SalI and SspI, ligated to the termination codon site of Fragment 1 digested with SalI, integrated into the SmaI site of pUC18 to construct the expression vector for the production of the present protein [pKOT245 (FIG. 4)] which was deposited (Accession Number Bikokenki FERM-P-P-14895) at the National Institute of Bioscience and Human-Technology (NIBH), Agency of Industrial Science and Technology located in 1-3, Higashi 1-chome, Tsukuba-shi, Tbaraki-ken, Japan on Apr. 14, 1995, and transferred to a deposit (Accession No. BIKOKEN-KI BP-5499) on Apr. 10, 1996 according to Budapest Treaty on the International Recognition of the Deposit of Microorganisms. The DNA of pKOT245 has a length of 3.7 kb. The expression vector for the present protein as constructed was determined for its base sequence by means of Pharmacia ALF DNA sequencer.

(3) Transformation

Transformation was performed according to the rubidium chloride method by Kushner et al. (Genetic Engineering, p. 17, Elsevier (1978)). That is to say, pKOT245 was migrated into a host *E. coli* W3110M according to the above-mentioned procedure to prepare the *E. coli* capable of producing the present protein.

2. Cultivation (1) Cultivation

The present protein producing *E. coli* was precultured in modified SOC medium (Bacto tryptone 20 g/l, Bacto yeast extract 5 g/l, NaCl 0.5 g/l, $MgCl_2.6H_2O$ 2.03 g/l, Glucose 3-6 g/l) and 100 ml of the mycelium suspension was added to 5 L of the productive medium (Bacto tryptone 5 g/l, Citric acid 4.3 g/l, $K_2HPO_4$ 4.675 g/l, $KH_2PO_4$ 1.275 g/l, NaCl 0.865 g/l, $FeSO_4.7H_2O$ 100 mg/l, $CuSO_4.5H_2O$) 1 mg/l, $MnSO_4.nH_2O$ 0.5 mg/l, $CaCl_2.2H_2O$ 2 mg/l, $Na_2B_4O_7.10H_2O$ 0.225 mg/l, $(NH_4)6Mo_7O_{24}.4H_2O$ 0.1 mg/l, $ZnSO_4.7H_2O$ 2.25 mg/l, $CoCl_2.6H_2O$ 6 mg/l, $MgSO_4.7H_2O$ 2.2 g/l, Thiamine HCl 5.0 mg/l, Glucose 3 g/l) and then cultured with stirring and aeration in a 10 L culture tank and isopropyl-β-D-thiogalactopyranoside was added at a concentration of 1 mM at the stage of a logarithmic growth phase ($OD_{550}$=5.0) and then cultivation was continued until the $OD_{550}$ reached 150. During the cultivation, the temperature was controlled to 32° C. and a pH value was adjusted to 7.15 by adding ammonia, while a dissolved oxygen concentration was controlled to 50% of air saturation by increasing a stirring speed to prevent any reduction in the dissolved oxygen concentration. On the other hand, cultivation was carried out by adding a 50% glucose solution at 0.2% concentrations using as a standard a rapid increase in the dissolved oxygen concentration in order to keep a high mycelium concentration.

(2) Preparation of *E. coli* Inclusion Body

The cultured broth obtained as above was centrifuged to recover the mycelium, which was then suspended in 25 mM Tris-HCl buffer containing 10 mM ethylenediaminetetraacetic acid (pH 7.3) and then bacteria were broken by means of a mycelium breaking apparatus (available from Gohlin Co., Inc.) and centrifuged again to recover the precipitate containing the inclusion body.

3. Purification (1) Solubilization of *E. coli* Inclusion Body

The *E. coli* inclusion body was washed thrice with 1% Triton X-100 and then centrifuged at 3,000×g at 4° C. for 30 minutes. The precipitate thus obtained was solubilized under ultasonification with 20 mM Tris-HCl buffer, pH 8.3, 8 M urea, 10 mM DTT and 1 mM EDTA.

(2) Purification of Monomer

The solubilized liquid thus obtained was centrifuged at 20,000×g at 4° C. for 30 minutes to recover the supernatant. The resultant supernatant was passed through SP-Sepharose FF (Pharmacia) which had been equilibrated with 20 mM Tris-HCl buffer (pH 8.3), 6 M urea, and 1 mM EDTA, washed with said solution and then eluted with said solution containing 0.5 M sodium chloride. To the eluate were added $Na_2SO_3$ and $Na_2S_4O_6$ at the respective final concentrations of 111 mM and 13 mM and sulfonation was carried out at 4° C. for 15 hours. The sulfonated solution was gel-filtrated with Sephacryl S-200 (Pharmacia) which had been equilibrated with 20 mM Tris-HCl buffer (pH 8.3), 6M urea, 0.2 M sodium chloride and 1 mM EDTA to obtain a single sulfonated protein monomer of the invention.

(3) Refolding

To a solution of the sulfonated protein monomer of the invention was added a 9 times volume of 50 mM Na-Glycine buffer (pH 9.8), 0.2 M sodium chloride, 16 mM CHAPS, 5 mM EDTA and 2 mM GSH (glutathione of reduced type) and 1 mM GSSG (glutathione of oxide type), and then the mixture was stirred at 4° C. for one day to perform refolding.

(4) Purification of Dimer

The sample was diluted into a two-times volume of purified water and then added by 6 N NaCl adjusting pH to approximately pH 7.4 and placed to isoelectric precipitation. The precipitation collected by contrifugation at 3,000×g for 20 minutes was solubilized in a solution with 30% acetonitrile containing 0.1% TFA. The solution was diluted into a two-times volume of purified water and loaded on RESOURCE RPC column (Pharmacia) of a reverse-phase HPLC which had been equilibrated with 25% acetonitrile containing 0.05% TFA, and then eluted with a linear gradient of 25-45% acetonitrile containing 0.05% TFA. The eluate was monitored at 280 nm absorbance. The purified homodimer protein fractions were collected and lyophilized by Speedback Concentrator (Servant Co.).

(5) Determination of Physico-chemical Properties of the Present Purified Protein (a) Analysis of N-terminal Amino Acid Sequence The present purified protein obtained as above was analyzed for the N-terminal amino acid sequence by means of an amino acid sequencer, Model 476A (Applied Biosystems) to confirm the amino acid sequence from the N-terminal up to the 30$^{th}$ amino acid as shown in SEQ ID NO.: 1 of The Sequence Listing.

(b) Analysis of Amino Acid Composition

The present purified protein obtained as above was investigated by means of amino acid analyzer [PICO TAG System (Waters Co., Ltd.)]. The results are shown in Table 3 wherein the numerical indication means the number of the amino acid residue per monomer.

TABLE 3

| AminoAcid | Practical No. | Estimated No. |
|---|---|---|
| Asx | 11.5 | 12 |
| Glx | 10.9 | 11 |
| Ser | 8.4 | 9 |
| Gly | 4.3 | 4 |
| His | 4.0 | 4 |
| Arg | 7.7 | 7 |
| Thr | 5.4 | 6 |
| Ala | 7.3 | 7 |
| Pro | 10.2 | 10 |
| Tyr | 2.9 | 3 |
| Val | 5.7 | 7 |
| Met | 5.1 | 4 |
| 1/2Cys | 2.6 | 7 |
| Ile | 4.9 | 6 |
| Leu | 10.0 | 10 |
| Phe | 4.0 | 4 |
| Lys | 5.9 | 6 |
| Trp | — | 2 |
| Sequence Length | | 119 |

—: undetectable (c) Analysis by Electrophoresis

The molecular weight of the present purified protein obtained above was confirmed by means of SDS-PAGE under non-reductive conditions to show a molecular weight of about 28 KDa.

It has been proven from the results shown in the aforesaid items (a), (b) and (c) that the present protein is a protein consisting of 119 amino acid residues simply starting from the N-terminal of Pro.

INDUSTRIAL UTILIZATION

The cartilage and bone morphogenetic repairing composition according to the invention can be applied to the affected site in the bone fracture therapy requiring no surgical operation in a simple and painless manner due to a high bio-absorption, a favorable affinity to the active ingredient, i.e., a bone morphogenetic protein, and a temperature dependent sol-gel reversible transition. Thus, the drug effect of a bone morphogenetic protein may be sustained and further a cartilage and bone morphogenetic repairing composition with less side-effects may be provided.

The invention claimed is:

1. A cartilage and bone morphogenetic repairing composition comprising a bone morphogenetic protein in a matrix material, wherein said matrix material consists of polyoxyethylene-polyoxypropylene glycol.

2. The cartilage and bone morphogenetic repairing composition as claimed in claim 1, wherein the molecular weight of polyoxypropylene as a constituent of said polyoxyethylene-polyoxypropylene glycol is about 1,500-4,000 Daltons and said polyoxyethylene-polyoxypropylene glycol has an ethylene oxide content of about 40-80% per molecule.

3. The cartilage and bone morphogenetic repairing composition as claimed in claim 2, wherein a concentration of said polyoxyethylene-polyoxypropylene glycol in an aqueous solution is about 10-50%.

4. The cartilage and bone morphogenetic repairing composition as claimed in claim 1, wherein said bone morphogenetic protein is BMP-2.

5. The cartilage and bone morphogenetic repairing composition as claimed in claim 1, wherein said bone morphogenetic protein is MP52.

6. A method for repairing a bone fracture, comprising locally administering the composition according to claim 1 to a patient in need of such treatment at the site of a bone fracture.

7. The method as claimed in claim 6, wherein a concentration of said polyoxyethylene-polyoxypropylene glycol in an aqueous solution is about 10-50%.

8. The method as claimed in claim 6, wherein said bone morphogenetic protein is BMP-2.

9. The method as claimed in claim 6, wherein said bone morphogenetic protein is MP52.

10. A method for inducing cartilage and/or bone morphogenesis, comprising locally administering the composition according to claim 1 to a patient in need of such treatment at the site of a cartilage or bone defect where cartilage and/or bone morphogenesis is desirable.

11. The method as claimed in claim 6, wherein a concentration of said polyoxyethylene-polyoxypropylene glycol in an aqueous solution is about 10-50%.

12. The method as claimed in claim 6, wherein said bone morphogenetic protein is BMP-2.

13. The method as claimed in claim 6, wherein said bone morphogenetic protein is MP52.

14. A composition comprising a bone morphogenetic protein in a matrix material, wherein said matrix material consists of polyoxyethylene-polyoxypropylene glycol.

* * * * *